United States Patent
Zilberman et al.

(10) Patent No.: US 11,623,105 B2
(45) Date of Patent: Apr. 11, 2023

(54) RADIOACTIVE SEED IMPLANTATION BY ABLATION CATHETER

(71) Applicant: Biosense Webster (Israel) Ltd., Yokneam (IL)

(72) Inventors: Israel Zilberman, Yokneam (IL); Assaf Govari, Haifa (IL); Gili Attias, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 626 days.

(21) Appl. No.: 16/707,572

(22) Filed: Dec. 9, 2019

(65) Prior Publication Data

US 2021/0170196 A1 Jun. 10, 2021

(51) Int. Cl.
*A61N 5/10* (2006.01)
*A61B 18/14* (2006.01)
*A61B 18/00* (2006.01)

(52) U.S. Cl.
CPC ........ *A61N 5/1007* (2013.01); *A61B 18/1492* (2013.01); *A61B 2018/00351* (2013.01); *A61B 2018/00577* (2013.01); *A61B 2218/002* (2013.01); *A61N 2005/1024* (2013.01)

(58) Field of Classification Search
CPC .......... A61N 5/1007; A61N 2005/1024; A61N 1/406; A61B 18/1492; A61B 2018/00351; A61B 2018/00577; A61B 2218/002; A61B 2090/062
See application file for complete search history.

(56) References Cited

U.S. PATENT DOCUMENTS 10,080,909 B2 * 9/2018 Brachman ............ A61N 5/1007
2006/0217587 A1   9/2006 DiCarlo et al.
2010/0234670 A1   9/2010 Shai et al.

* cited by examiner

*Primary Examiner* — Jung Kim
(74) *Attorney, Agent, or Firm* — Volpe Koenig

(57) ABSTRACT

Methods, apparatus, and systems for medical procedures are disclosed herein and include applying an ablation electrode of a catheter to a surface of a tissue area, providing a first energy to the ablation electrode applied on the surface of the tissue area to ablate the tissue area, inserting a catheter needle of the catheter to a first distance into the tissue area, through the surface of the tissue area, depositing, via the catheter needle, a first radioactive seed at the first distance, and damaging a second portion of the tissue area based on depositing the first radioactive seed at the first distance.

6 Claims, 8 Drawing Sheets

RADIOACTIVE SEED IMPLANTATION BY ABLATION CATHETER

FIELD OF INVENTION

The present application provides systems, apparatuses, and methods for improving medical procedures.

BACKGROUND

Medical conditions such as cardiac arrhythmia (e.g., atrial fibrillation (AF)) are often diagnosed and treated via intra-body procedures. For example, electrical pulmonary vein isolation (PVI) from the left atrial (LA) body is performed using ablation for treating AF. PVI, and many other minimally invasive catheterizations, cause damage to organ tissue to prevent electrical activity through the organ tissue.

Intra-body organs include tissue that can vary within different portion of the intra-body organ and that can also vary within different areas of chambers of the intra-body organ, such as different chambers of the heart.

SUMMARY

Methods, apparatus, and systems for medical procedures are disclosed herein and include applying an ablation electrode of a catheter to a surface of a tissue area, providing a first energy to the ablation electrode applied on the surface of the tissue area to ablate the tissue area, inserting a catheter needle of the catheter to a first distance into the tissue area, through the surface of the tissue area, depositing, via the catheter needle, a first radioactive seed at the first distance, and damaging a second portion of the tissue area based on depositing the first radioactive seed at the first distance.

Methods, apparatus, and systems for medical procedures are disclosed herein and include ablating a tissue area by direct contact between a catheter electrode and a surface of the tissue area, determining that a threshold thickness of the tissue area is not ablated, determining a first distance from the surface of the tissue area to a first un-ablated portion of the tissue area, inserting a catheter needle, of the catheter, to a first extension state, the first extension state based on the first distance and depositing, via the catheter needle, a first radioactive seed when the catheter needle is at the first extension state.

Methods, apparatus, and systems for medical procedures are disclosed herein and include a device that includes an ablation electrode, a catheter needle, the catheter needle including a first hollow portion, a movement mechanism configured to extend the first hollow portion past an initial state, a radioactive seed reservoir configured to hold a plurality of radioactive seeds and a release mechanism configured to provide at least a subset of the plurality of radioactive seeds from the radioactive seed reservoir to the first hollow portion.

BRIEF DESCRIPTION OF THE DRAWINGS

A more detailed understanding can be had from the following description, given by way of example in conjunction with the accompanying drawings wherein.

DETAILED DESCRIPTION

Figure 1:
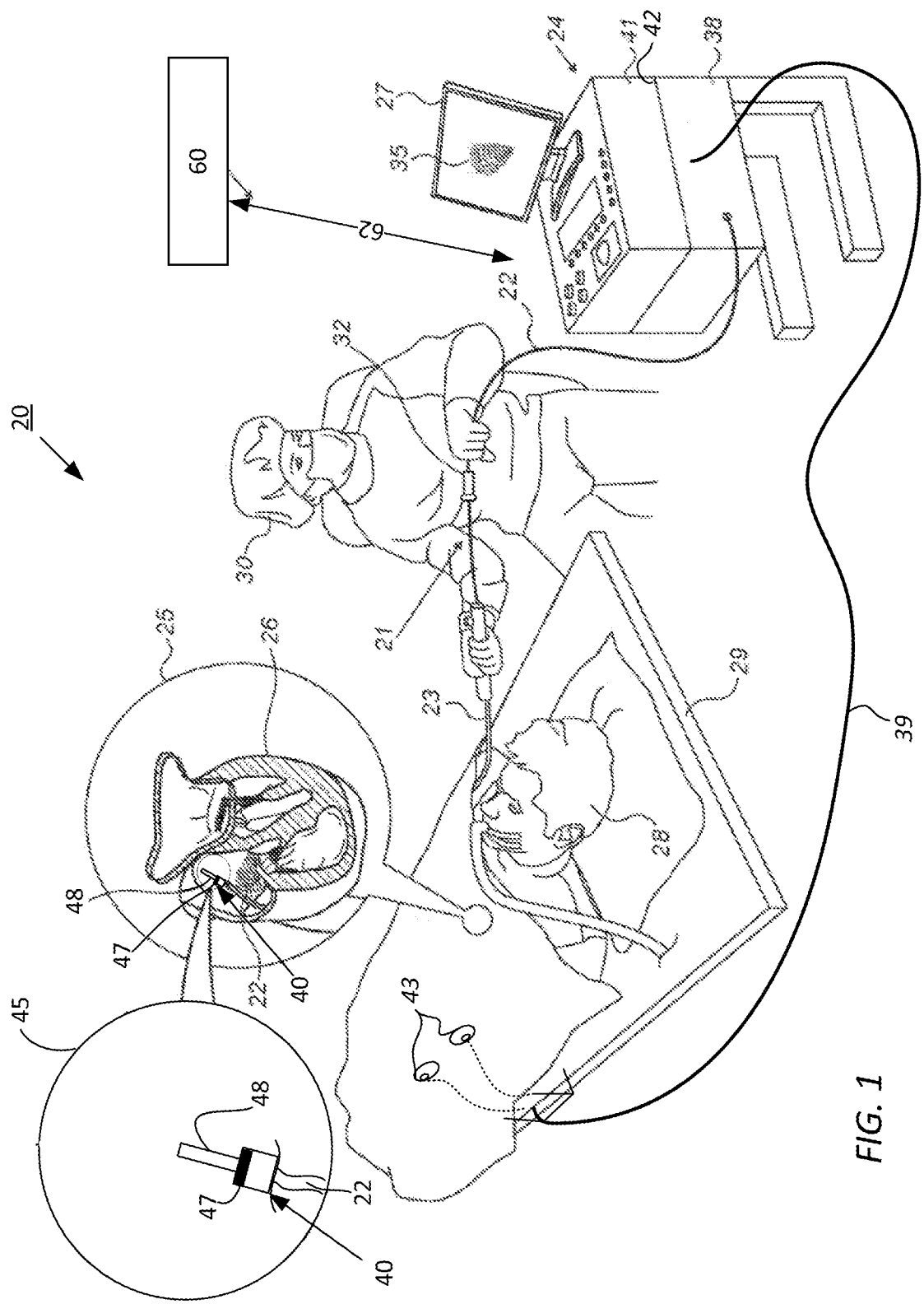
FIG. 1 is a diagram of an exemplary system for implementation of the disclosed subject matter.

According to implementations of the disclosed subject matter, tissue that is part of an intra-body organ may be selectively damaged to prevent electrical propagation through the tissue. The tissue may be selectively damaged using a combination of thermal energy as well as by using radioactive seeds, as disclosed herein.

Thermal ablation, such as radio frequency (RF) based ablation, may ablate all or a portion of a tissue area of an intra-body organ such as a heart. During thermal ablation, one or more ablation electrodes of a catheter may be placed in contact with the surface of the tissue area and energy may be applied to the one or more electrodes. Applying the energy to the one or more electrodes may ablate at least a portion of the tissue area such that the ablated portion of the tissue area may start at the surface of the tissue area and extend into a thickness of the tissue area away from the surface of the tissue area. The extent of the ablation may be based on the type of catheter, the type of the one or more electrodes, the tissue thickness, the tissue type, or the like. The ablation may scar, destroy, or otherwise damage ("damage") the given portion of the tissue area that is ablated such that the given portion of the tissue area may not conduct electricity.

According to an embodiment, a tissue area may be selected for damage to prevent electrical activity through the tissue area. The tissue area may be selected for damage based on any applicable reason such as to prevent atrial fibrillation (AFib) and other cardiac arrhythmias, prevent a rotor signal within an area of the heart, prevent complex fractionated atrial electrograms (CFAE), block ganglionated plexi, or the like. The tissue area may have a surface and a thickness. Thermal energy may be applied from the surface of the tissue area and may damage a portion of a tissue area including the surface and through a thickness of the tissue area. However, the damage to the tissue area caused by the thermal ablation may not extend through the entire thickness of the tissue area. Notably, certain tissue areas such as those in the ventricular tachycardia (VT) may have properties, such as tissue thickness or tissue density, which may prevent the damage from the thermal ablation to extend past a certain thickness of the tissue area. Accordingly, electricity may pass through the unablated portion of the tissue area after the thermal ablation (i.e., from the non-damaged portion of the tissue area).

According to embodiments of the disclosed subject matter, an ablation catheter may include at least one ablation electrode (e.g., for thermal ablation) as well as a catheter needle. The catheter needle may include a hollow portion (i.e., the needle itself) and a movement mechanism that enables the catheter needle to extend the hollow portion past an initial un-extended extension state. The initial un-extended extension state may be a position of the hollow portion that is flush with a distal surface of the catheter or may be a position within the catheter that does not reach the distal surface of the catheter. Upon activation, the movement mechanism may extend the hollow portion past the initial un-extended extension state and through the distal end of the catheter and further through the surface of the tissue area, up to a given thickness within the tissue area. A radioactive seed reservoir may hold one or more radioactive seeds that may be provided to the hollow portion upon activation of a release mechanism. Accordingly, the radioactive seeds may be deposited into the tissue area at the given thickness, via the hollow portion of the catheter needle. The radioactive seeds may damage a portion of the tissue area that extends past the tissue area that was damaged by the thermal ablation such that more or all of the thickness of the tissue area is damaged.

FIG. 1 is a diagram of an exemplary system 20 in which one or more features of the disclosure subject matter can be implemented. System 20 may include components, such as a catheter 40, that are configured to damage tissue areas of an intra-body organ. The catheter 40 may also be further configured to obtain biometric data. Although catheter 40 is shown to be a point catheter, it will be understood that a catheter of any shape that includes one or more elements (e.g., electrodes) may be used to implement the embodiments disclosed herein. System 20 includes a probe 21, having shafts that may be navigated by a physician 30 into a body part, such as heart 26, of a patient 28 lying on a table 29. According to embodiments, multiple probes may be provided, however, for purposes of conciseness, a single probe 21 is described herein but it will be understood that probe 21 may represent multiple probes. As shown in FIG. 1, physician 30 may insert shaft 22 through a sheath 23, while manipulating the distal end of the shafts 22 using a manipulator 32 near the proximal end of the catheter 40 and/or deflection from the sheath 23. As shown in an inset 25, catheter 40 may be fitted at the distal end of shafts 22. Catheter 40 may be inserted through sheath 23 in a collapsed state and may be then expanded within heart 26. Cather 40 may include at least one ablation electrode 47 and a catheter needle 48, as further disclosed herein.

According to embodiments, catheter 40 may be configured to ablate tissue areas of a cardiac chamber of heart 26. Inset 45 shows catheter 40 in an enlarged view, inside a cardiac chamber of heart 26. As shown, catheter 40 may include at least one ablation electrode 47 and a catheter needle 48 coupled onto the body of the catheter. FIG. 1 and, specifically, inset 45 show the catheter needle 48 in an extended state. However, as disclosed herein, the catheter needle 48 may be in an un-extended state and may extend to the extended state, as shown in FIG. 1, to deposit one or more radioactive seeds. According to other embodiments, multiple elements may be connected via splines that form the shape of the catheter 40. One or more other elements (not shown) may be provided and may be any elements configured to ablate or to obtain biometric data and may be electrodes, transducers, or one or more other elements.

According to embodiments disclosed herein, the ablation electrodes, such as electrode 47, may be configured to provide energy to tissue areas of an intra-body organ such as heart 26. The energy may be thermal energy and may cause damage to the tissue area starting from the surface of the tissue area and extending into the thickness of the tissue area.

According to embodiments disclosed herein, biometric data may include one or more of LATs, electrical activity, topology, bipolar mapping, dominant frequency, impedance, or the like. The local activation time may be a point in time of a threshold activity corresponding to a local activation, calculated based on a normalized initial starting point. Electrical activity may be any applicable electrical signals that may be measured based on one or more thresholds and may be sensed and/or augmented based on signal to noise ratios and/or other filters. A topology may correspond to the physical structure of a body part or a portion of a body part and may correspond to changes in the physical structure relative to different parts of the body part or relative to different body parts. A dominant frequency may be a frequency or a range of frequency that is prevalent at a portion of a body part and may be different in different portions of the same body part. For example, the dominant frequency of a pulmonary vein of a heart may be different than the dominant frequency of the right atrium of the same heart. Impedance may be the resistance measurement at a given area of a body part.

As shown in FIG. 1, the probe 21, and catheter 40 may be connected to a console 24. Console 24 may include a processor 41, such as a general-purpose computer, with suitable front end and interface circuits 38 for transmitting and receiving signals to and from catheter, as well as for controlling the other components of system 20. In some embodiments, processor 41 may be further configured to receive biometric data, such as electrical activity, and determine if a given tissue area conducts electricity. According to an embodiment, the processor may be external to the console 24 and may be located, for example, in the catheter, in an external device, in a mobile device, in a cloud-based device, or may be a standalone processor.

As noted above, processor 41 may include a general-purpose computer, which may be programmed in software to carry out the functions described herein. The software may be downloaded to the general-purpose computer in electronic form, over a network, for example, or it may, alternatively or additionally, be provided and/or stored on non-transitory tangible media, such as magnetic, optical, or electronic memory. The example configuration shown in FIG. 1 may be modified to implement the embodiments disclosed herein. The disclosed embodiments may similarly be applied using other system components and settings. Additionally, system 20 may include additional components, such as elements for sensing electrical activity, wired or wireless connectors, processing and display devices, or the like.

According to an embodiment, a display connected to a processor (e.g., processor 41) may be located at a remote location such as a separate hospital or in separate healthcare provider networks. Additionally, the system 20 may be part of a surgical system that is configured to obtain anatomical and electrical measurements of a patient's organ, such as a heart, and performing a cardiac ablation procedure. An example of such a surgical system is the Carte system sold by Biosense Webster.

The system 20 may also, and optionally, obtain biometric data such as anatomical measurements of the patient's heart using ultrasound, computed tomography (CT), magnetic resonance imaging (MRI) or other medical imaging techniques known in the art. The system 20 may obtain electrical measurements using catheters, electrocardiograms (EKGs) or other sensors that measure electrical properties of the heart. The biometric data including anatomical and electrical measurements may then be stored in a memory 42 of the mapping system 20, as shown in FIG. 1. The biometric data may be transmitted to the processor 41 from the memory 42.

Alternatively, or in addition, the biometric data may be transmitted to a server 60, which may be local or remote, using a network 62. Similarly, ultrasound slices may be transmitted to a server 60, which may be local or remote, using a network 62.

Network 62 may be any network or system generally known in the art such as an intranet, a local area network (LAN), a wide area network (WAN), a metropolitan area network (MAN), a direct connection or series of connections, a cellular telephone network, or any other network or medium capable of facilitating communication between the mapping system 20 and the server 60. The network 62 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 62.

In some instances, the server 62 may be implemented as a physical server. In other instances, server 62 may be implemented as a virtual server a public cloud computing provider (e.g., Amazon Web Services (AWS)®).

Control console 24 may be connected, by a cable 39, to body surface electrodes 43, which may include adhesive skin patches that are affixed to the patient 30. The processor, in conjunction with a current tracking module, may determine position coordinates of the catheter 40 inside the body part (e.g., heart 26) of a patient. The position coordinates may be based on impedances or electromagnetic fields measured between the body surface electrodes 43 and the electrode 48 or other electromagnetic components of the catheter 40. Additionally or alternatively, location pads may be located on the surface of bed 29 and may be separate from the bed 29.

Processor 41 may comprise real-time noise reduction circuitry typically configured as a field programmable gate array (FPGA), followed by an analog-to-digital (A/D) ECG (electrocardiograph) or EMG (electromyogram) signal conversion integrated circuit. The processor 41 may pass the signal from an A/D ECG or EMG circuit to another processor and/or can be programmed to perform one or more functions disclosed herein.

Control console 24 may also include an input/output (I/O) communications interface that enables the control console to transfer signals from, and/or transfer signals to electrode 47.

During a procedure, processor 41 may facilitate the presentation of a body part rendering 35 and/or an ultrasound slice 37 to physician 30 on a display 27, and store data representing the body part rendering 35 in a memory 42. Memory 42 may comprise any suitable volatile and/or non-volatile memory, such as random-access memory or a hard disk drive. In some embodiments, medical professional 30 may be able to manipulate a body part rendering 35 using one or more input devices such as a touch pad, a mouse, a keyboard, a gesture recognition apparatus, or the like. For example, an input device may be used to change the position of catheter 40 such that rendering 35 is updated. In alternative embodiments, display 27 may include a touchscreen that can be configured to accept inputs from medical professional 30, in addition to presenting a body part rendering 35.

Figure 2:
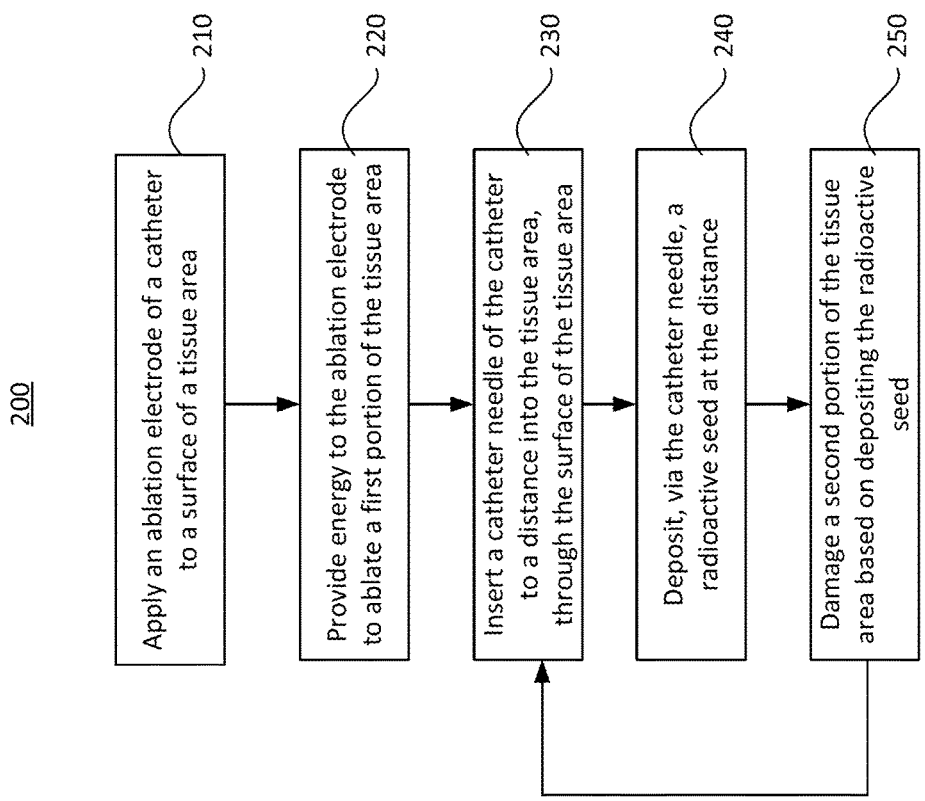
FIG. 2 is a flowchart of a process for damaging a tissue area.

FIG. 2 is a flowchart of a process 200 for damaging a tissue area to prevent electrical activity through the tissue area. At step 210 of the process 200, ablation electrodes, such as ablation electrode 47 of FIG. 1, of an ablation catheter, such as catheter 40, may be applied to the surface of a tissue area.

Figure 3:
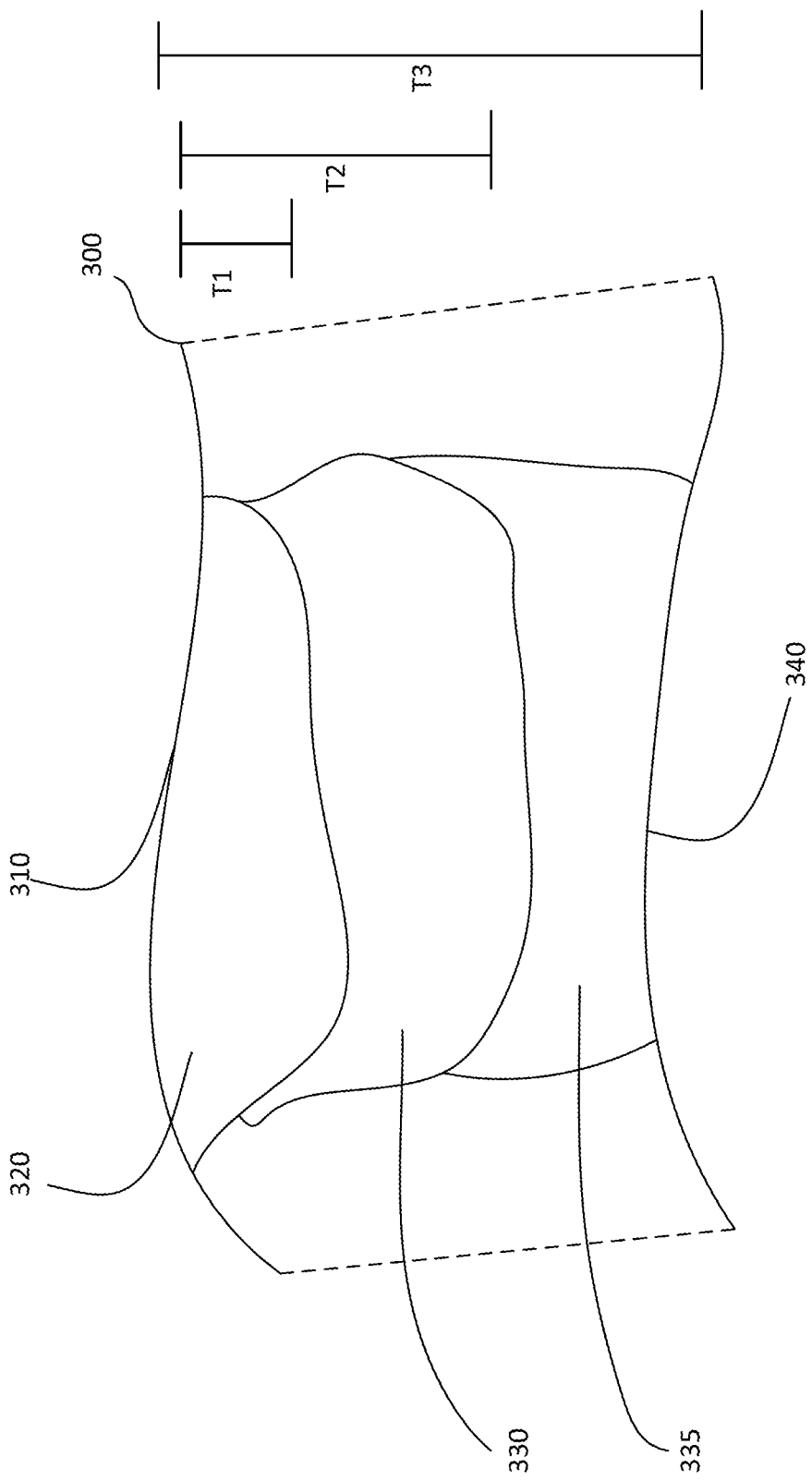
FIG. 3 is an illustration of an tissue area with corresponding thicknesses.

FIG. 3 shows an example tissue area 300 which may be the tissue area of a chamber of an intra-body organ, such as heart 26 of FIG. 1. The tissue area 300 may be, for example, part of the VT of a heart. The tissue area 300 may have an overall thickness of T3 which may include intermediate thicknesses for different segments of the tissue area 300. As shown, a first segment 320 may extend from the surface 310 to a thickness of T1 in a direction facing away from the surface 310. A second segment 330 may generally extend from the thickness T1 to a thickness T2. A third segment 335 may generally extend from the thickness T2 to the thickness T3. The surface 310 of the tissue area 300 may be the endocardium surface of the tissue area. The thickness T1 and/or T2 may correspond to the myocardium portion of the tissue area 300. The surface of the tissue area 300 that is opposite the surface 310 may be a surface 340 which corresponds to the epicardium of the tissue area 300.

Figure 4C:
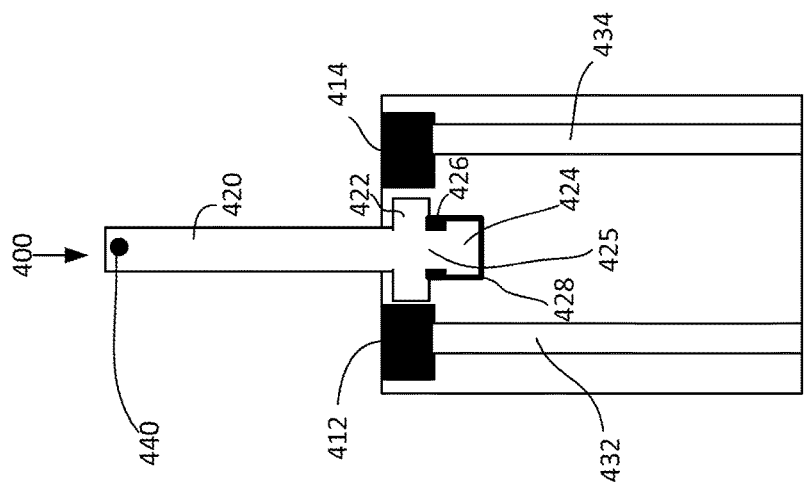
FIG. 4C is another illustration of the catheter of FIG. 4A with the catheter needle at a second extension state.
Figure 4B:
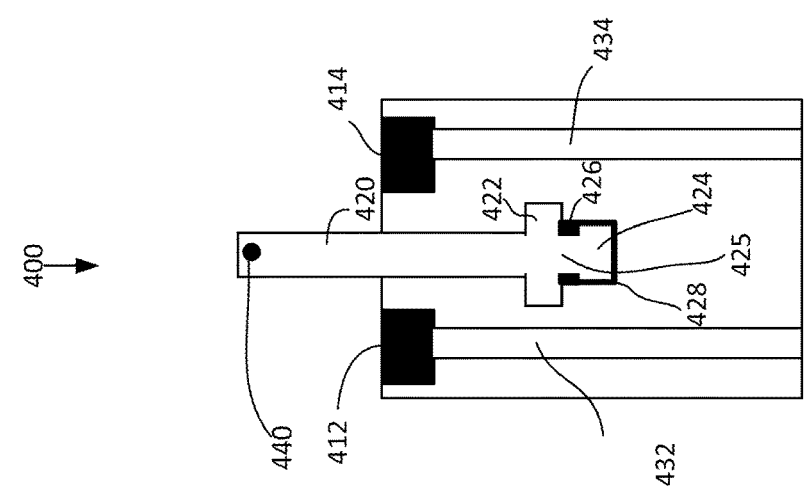
FIG. 4B is another illustration of the catheter of FIG. 4A with the catheter needle at a first extension state.
Figure 4A:
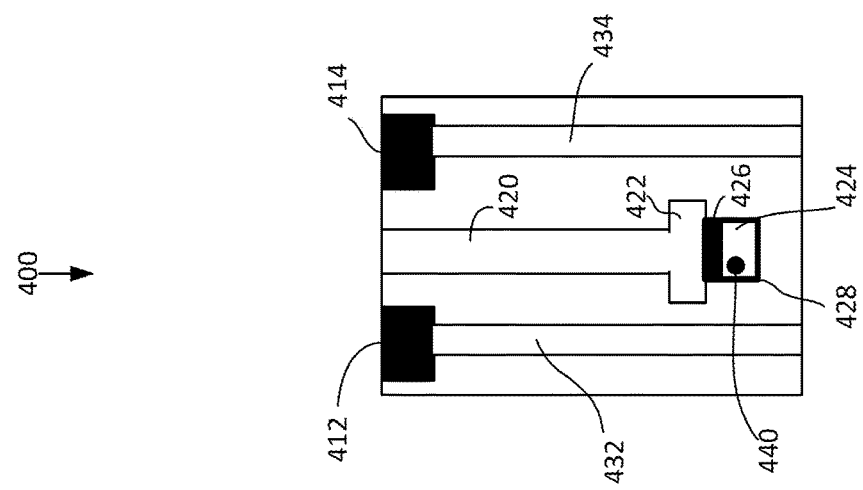
FIG. 4A is an illustration of a catheter with a catheter needle at an un-extended extension state.

FIGS. 4A-4C show an ablation catheter 400 that includes a catheter needle 420 at an un-extended extension state P1 (i.e., FIG. 4A), at a first extension state P2 (i.e., FIG. 4B), and a second extension state P3 (i.e., FIG. 4C). As shown in FIGS. 4A-4C, the catheter 400 may also include ablation electrodes 412 and 414, irrigation hollow portions 432 and 434. The catheter needle 420 may be, for example, a 27 gauge needle. The catheter needle 420 may be attached to a movement mechanism 422, a radioactive seed reservoir 424, and a release mechanism 426. The radioactive seed reservoir 424 may be fully or partially encapsulated by a radioactive seal 428. As shown in FIG. 4A, one or more radioactive seed(s) 440 may be stored in the radioactive seed reservoir 424. The first extension state P2 may be any intermediate extension state that is between the un-extended state P1 and the second extension state P3 and may be, for example, between 4 mm-8 mm. The second extension state P3 may be the longest or near longest extension state that the catheter 400 and catheter needle 420 are configured to extend towards and may be, for example 12 mm or greater.

The catheter needle 420 may be made of any applicable material, such as a metal, metal alloy, plastic, a combination thereof, or the like. The catheter needle 420 may include a hollow portion such that the inside of the catheter needle 420 is hollow. The hollow portion of the catheter needle 420 may have a radius that is larger than the radius and/or width of the radioactive seed 440 such that the radioactive seed 440 is able to pass through the catheter needle 420. The tip of the catheter needle 420 may be sharp such that it is configured to pierce the through the surface of a tissue area, such as tissue area 300 of FIG. 3 and through the thickness of the tissue area 300.

As shown in FIG. 4B and FIG. 4C, the catheter needle 420 may extend from the un-extended state P1 of FIG. 4A to a first extension state P2 or a second extension state P3. When the catheter needle 420 is in the first extension state P2 and second extension state P3, a tip of the catheter needle 420 may extend past a distal surface of the catheter 400, the distal surface corresponding to the surface of the catheter 400 that is proximally closest to the ablation electrodes 412 and 414 in FIGS. 4A-4C. Although the tip of the catheter needle 420 is shown as a flat tip, it will be understood that the tip may be a sharp tip such that a portion of the tip may protrude past a different portion of the tip to enable the catheter needle 420 to pierce through the surface and thickness of a tissue area.

The catheter needle 420 may change from an un-extended state P1, to a first extension state P2 and/or a second extension state P3 by a force provided by the movement mechanism 422. The force may be a frictional force, electrical force, kinetic force, or a combination thereof. For example, a processor, such as processor 41 may provide a signal to the catheter 400 and the movement mechanism may apply a force on the catheter needle 420 based on the signal. Although FIGS. 4B and 4C show that the movement mechanism 422 physically moves as the catheter needle 420 changes states, it will be understood that the movement mechanism 422 may physically stay in the same position while applying a force to change the state of the catheter needle 420. According to an embodiment, the movement mechanism 422, radioactive seed reservoir 424, and/or release mechanism 426 may be external to the housing of the catheter 400. It will also be understood that the techniques disclosed herein may be implemented without a movement mechanism 422, release mechanism 426, and/or radioactive seal 428.

The irrigation hollow portions 432 and 434 may provide fluid to or near the ablation electrodes 412 and 414 and may enable the ablation electrodes 412 and 414 to manage heat during or after activation. According to an embodiment, the irrigation hollow portions 432 and 434 may provide heat management of a tissue area, such as tissue area 300 of FIG. 3. Although two irrigation hollow portions 432 and 434 are shown, it will be understood that any number of irrigation hollow portions (e.g., 1, 3, etc.) may be provided. It will also be understood that the techniques disclosed herein may be implemented without any irrigation hollow portions, according to an embodiment. Further, it will be understood that the irrigation hollow portion 412 and/or 414 may be shaped or positioned different than as shown herein.

Although FIGS. 4A-4C show two ablation electrodes 412 and 414, it will be understood that any number of ablation electrodes (e.g., 1, 3, etc.) may be part of the catheter 400. As an example, the entire distal surface, as disclosed herein, of catheter 400 may include an ablation electrode.

The release mechanism 426 may contain one or more radioactive seeds, such as radioactive seed 440, within the radioactive seed reservoir 424 until the radioactive seeds are to be deposited within a tissue area, as further disclosed herein. As shown in FIGS. 4B and 4C, when the catheter needle 420 is in an extended state such as the first extension state P2 or second extension state P3, the release mechanism 426 may release the radioactive seeds, such as radioactive seed 440 from the radioactive seed reservoir 424. For example, the radioactive seeds may be released such that they can traverse through gap 425 in the release mechanism 426, into the hollow portion of the catheter needle 420 and, further, into a tissue area via the catheter needle 420.

It will also be understood that although a single radioactive seed 440 is provided in FIGS. 4A-4C and disclosed herein, the techniques disclosed herein may be implemented using a plurality of radioactive seeds.

According to embodiments of the disclosed subject matter, a tissue area, such as tissue area 300 of FIG. 3, may be identified as a problem tissue area and marked for damage. The tissue area 300 may be identified as a problem tissue area such that, for example, the electrical activity generated at tissue area 300 may be unwanted electrical activity. For example, the electrical activity generated at tissue area 300 may cause or increase the probability of AFib.

Figure 5A:
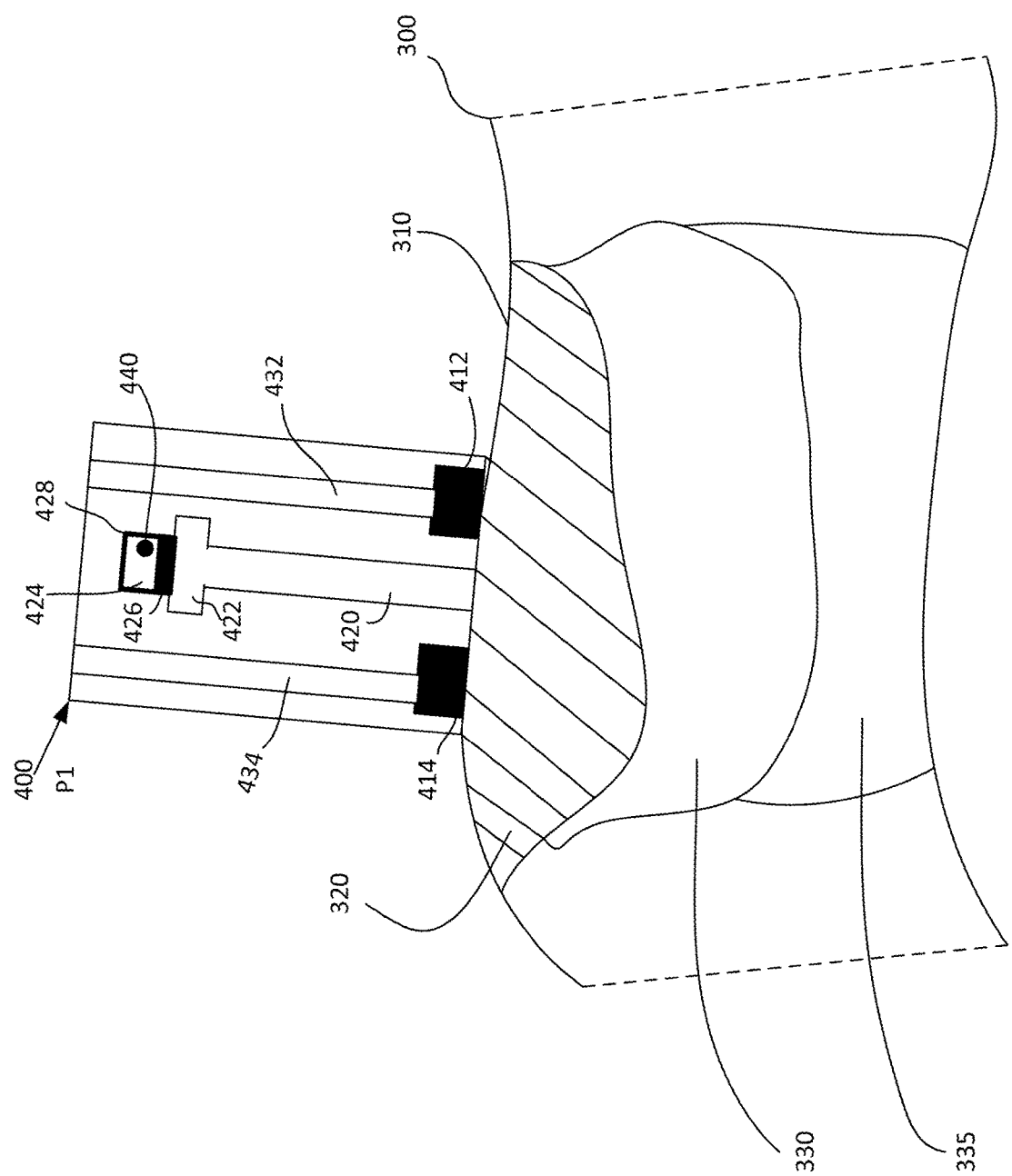
FIG. 5A is an illustration of the catheter of FIG. 4A over the tissue area of FIG. 3.
Figure 5B:
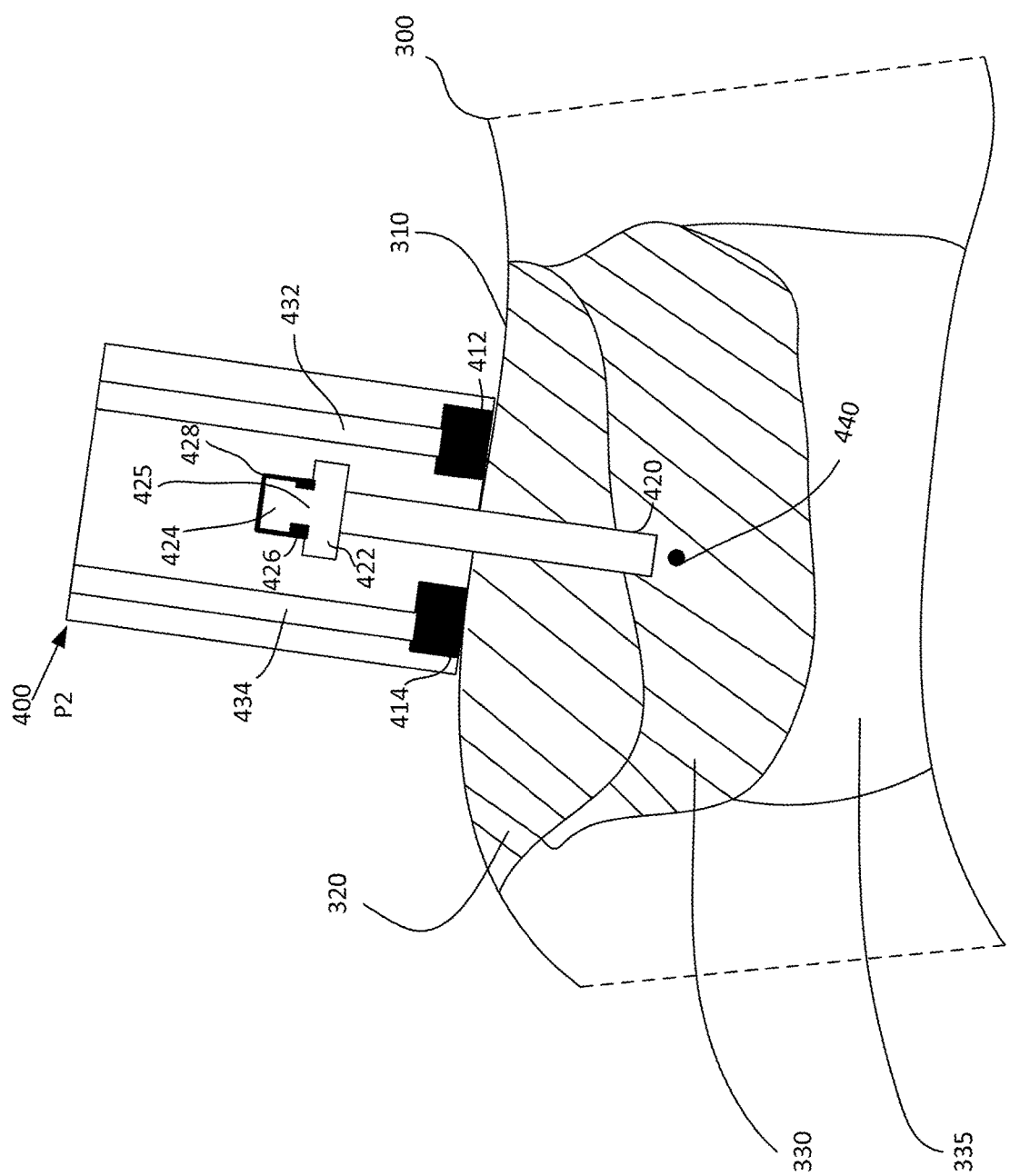
FIG. 5B is an illustration of the catheter of FIG. 4B over the tissue area of FIG. 3.
Figure 5C:
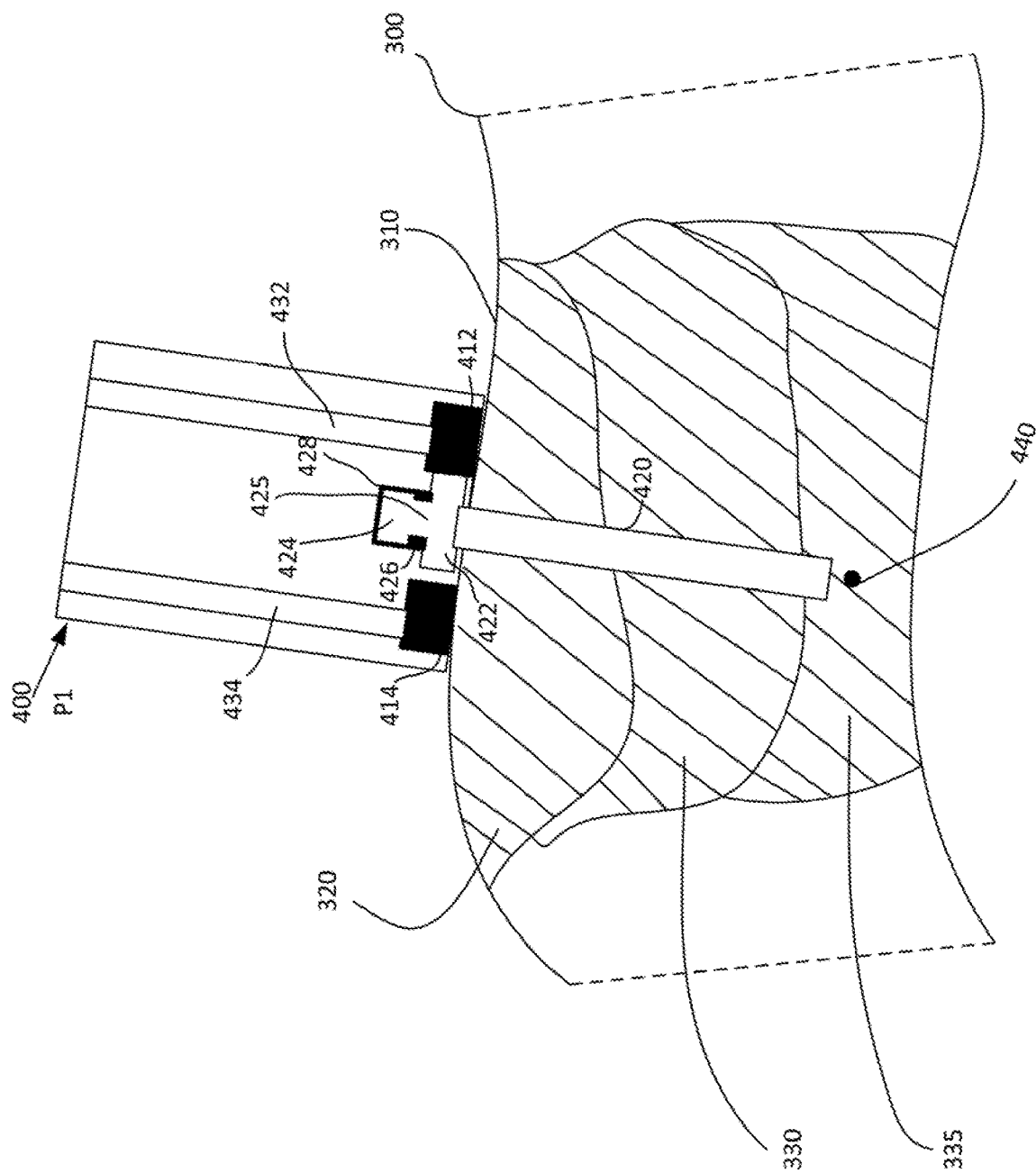
FIG. 5C is an illustration of the catheter of FIG. 4C over the tissue area of FIG. 3.

Referring back to FIG. 2, at step 210 of the process 200, ablation electrodes of an ablation catheter may be applied to the surface of a tissue area (e.g., via tenuous tip-tissue contact). FIGS. 5A-5C show the tissue area 300 of FIG. 3 and the catheter 400 of FIGS. 4A-4C at different extension states P1 (FIG. 5A), P2 (FIG. 5B) and P3 (FIG. 5C). For conciseness, not all components of the catheter 400 and/or tissue area 300 that are referenced in FIGS. 3-4C herein are disclosed again in reference to FIGS. 5A-5C, unless specifically addressed. It will be understood that the catheter 400 and the tissue area 300 of FIGS. 3-4C include components, areas, and/or features as disclosed in the FIGS. 3-4C and may also apply to the disclosure provided in reference to FIGS. 5A-C.

At step 210 of the process 200, as shown in FIG. 5A, the catheter 400 may be positioned such that ablation electrodes 412 and 414 are in contact with the surface 310 of the tissue area 300. According to embodiment, one or more signals may be sensed by catheter 400 and may be provided to processor (e.g., processor 41). Such signals may be used to determine the quality of the contact between the catheter 400 and/or the ablation electrodes 412 and 414 with the surface 310 of the tissue area 300. The position of the catheter 400 may be adjusted to ensure optimal contact between the catheter 400 and/or the ablation electrodes 412 and 414 with the surface 310 of the tissue area 300.

At step 220 of process 200 of FIG. 2, energy may be provided to the ablation electrodes 412 and 414 and the energy may cause the ablation electrodes 412 and 414 to ablate at least a portion of the tissue area 300. As an example, the ablation electrodes may be used to perform radiofrequency (RF) ablation such that RF energy is applied to heat and/or otherwise energize the tissue area 300. The RF energy may be applied when energy is provided to the ablation electrodes 412 and 414. The energy provided to the ablation electrodes 412 and 414 may be converted and/or transferred to the tissue area 300 and into a thickness of the tissue area 300. At least a portion of the tissue area 300 that receives a portion of energy from ablation electrodes 412 and 414 may be ablated such that the effected tissue area is damaged and no longer conducts electricity.

As shown in FIG. 5A, after step 220 of process 200 of FIG. 2, a first segment 320 of the tissue area 300 may be damaged as indicated by the dashed lines provided within the first segment 320 in FIG. 5A. The tissue within the first segment 320 may be damaged due to the energy transferred from the ablation electrodes 412 and 414. To clarify, energy provided by the electrodes 412 and 414 may be received at the surface 310 of the tissue area 300 and may further extend into the thickness of the tissue area 300 corresponding to the first segment 320. As shown in FIG. 5A, as a result of the thickness and/or other properties of the tissue area, the catheter 400, the ablation electrodes 412 and 414, and/or one or more other factors, the damage to the tissue caused by the energy provided at step 220 may not extend through the entire thickness of the tissue area 300. Notably, the tissue in the second segment 330 and the third segment 335 of the tissue area 300 may not be damaged. For example, the ablation at step 220 may correspond to inadequate RF energy transfer such that the entire tissue area 300 is not damaged.

At step 230 of the process 200 of FIG. 2, the catheter needle 420 of the catheter 400 may be inserted from the surface 310 to a first distance into the tissue area 300, as shown in FIG. 5B. As shown, the needle 420 may extend into the second segment 330 of the tissue area 300 by piercing the surface 310 and extending through the first segment 320 and into the second segment 330 of the tissue area 300. As shown in FIG. 5B, the catheter 400 and catheter needle 420 may be at the first extension state P2, as described regarding FIG. 4B. As disclosed herein, the catheter needle 420 may extend from the un-extended extension state P1 to the first extension state P2 as a result of a signal provided to the movement mechanism 422 that causes the hollow portion of the catheter needle 420 to change its position from the first un-extended extension state P1, as shown in FIG. 5A, to the first extension state P2, as shown in FIG. 5B. The distance that the catheter needle 420 extends into the thickness of the tissue area 300 may be pre-determined, or may be provided by a processor, such as processor 41 of FIG. 1, via a signal provided to the catheter 400.

At step 240 of the process 200 of FIG. 2, the radioactive seed 440 may be deposited, via the catheter needle 420, into a thickness of the tissue area 300. The radioactive seed 440 may be released from the radioactive seed reservoir 424 by the release mechanism 426, and may traverse through the gap 425 into the hollow portion of the catheter needle 420, such that the radioactive seed is deposited into a portion of the second segment 330 of the tissue area 300. Notably, the radioactive seed 440 may be deposited into a portion (e.g., the second segment 330) of the tissue area 300 that is either not damaged by the ablation caused by the energy expended through ablation electrodes 412 and 414 at step 220 of the process 200 or may be near such a not damaged portion of the tissue area 300. The radioactive seed 440 may have properties, as further disclosed herein, that may cause tissue area proximate to the radioactive seed 440 to be damaged, at step 250 of the process 200, via non-transmural lesion. As shown in FIG. 5B, the second segment 330 of the tissue area 300 may be damaged as a result of depositing the radioactive seed 440 at or near the second segment 330 of the tissue area 300.

As shown in FIG. 3, the tissue area 300 may have an overall thickness T3. As shown in FIG. 5B, a radioactive seed deposited at or around the thickness T2 corresponding to the second segment 330 of tissue area 330 may damage the tissue area corresponding to the second segment 330. However, the tissue area corresponding to the third segment 335 may not be damaged such that this area may conduct electricity even after the ablation at step 220 and the damage caused by the radioactive seed at step 230. Accordingly, part of the process 200 may be repeated to ensure that the entire thickness T3 of the tissue area 300 is damaged to prevent electrical activity from being conducted at and/or through the tissue area 300.

Accordingly, after step 250 of the process 200 of FIG. 0.2, step 230 of the process 200 may be repeated at a different thickness. At step 230, the catheter needle 420 of the catheter 400 may be inserted from the surface 310 to a second distance into the tissue area 300, as shown in FIG. 5C. As shown, the needle 420 may extend into the third segment 335 of the tissue area 300 by piercing the surface 310 and extending through the first segment 320, the second segment 330, and into the third segment 335 of the tissue area 300. As shown in FIG. 5C, the catheter 400 and catheter needle 420 may be at the second extension state P3, as described regarding FIG. 4C. As disclosed herein, the catheter needle 420 may extend from the un-extended extension state P1, to the first extension state P2, and to the third extension state P3 as a result of a signal provided to the movement mechanism 422 that causes the hollow portion of the catheter needle 420 to change its position from the first un-extended extension state P1, as shown in FIG. 5A, to the second extension state P3, as shown in FIG. 5C. The distance that the catheter needle 420 extends into the thickness of the tissue area 300 may be pre-determined, and/or may be provided by a processor, such as processor 41 of FIG. 1, via a signal provided to the catheter 400.

Figure 6:
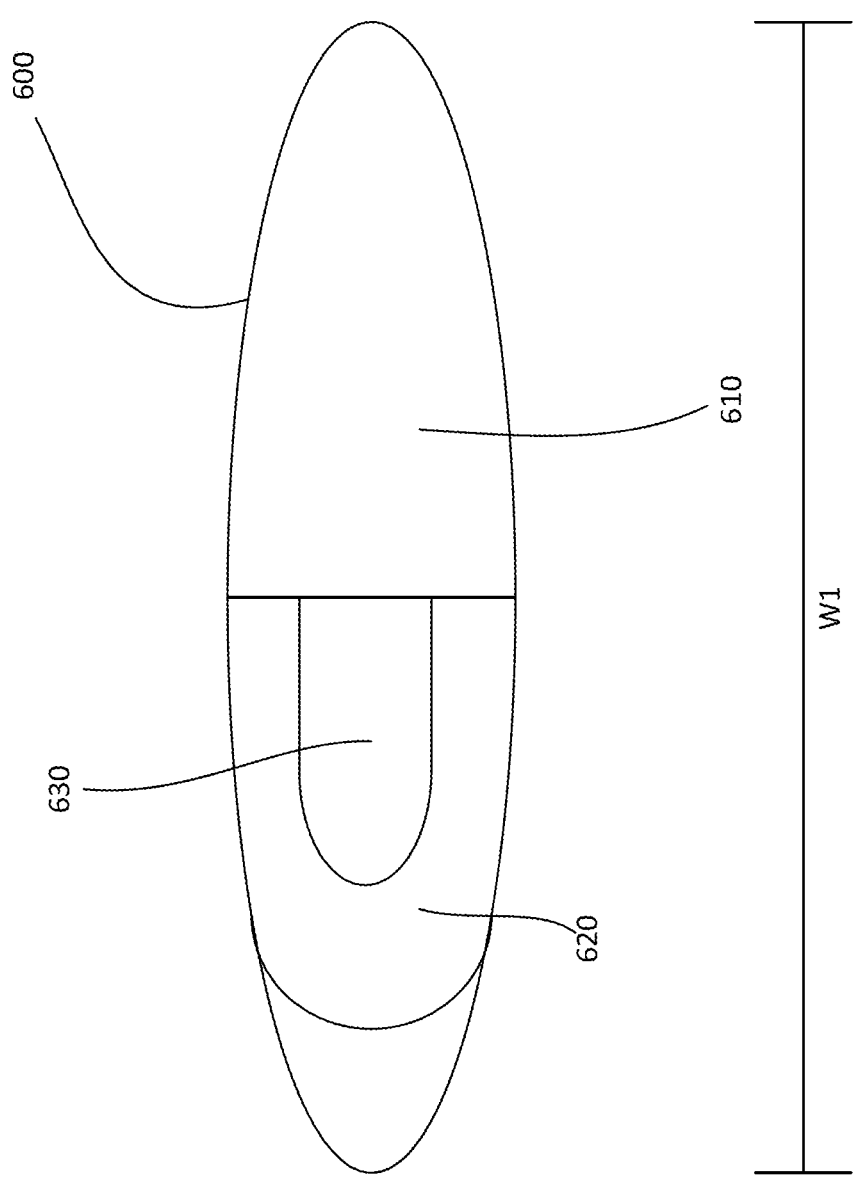
FIG. 6 is an illustration of a radioactive seed.

At step 240 of the process 200 of FIG. 2, the radioactive seed 440 may be deposited, via the catheter needle 420, into or near the third segment 335 of the tissue area 300. The radioactive seed 440 may be released from the radioactive seed reservoir 424 by the release mechanism 426, and may traverse through the gap 425 into the hollow portion of the catheter needle 420, such that the radioactive seed is deposited into a portion of the third segment 335 of the tissue area 300. Notably, the radioactive seed 440 may be deposited into or near a portion (e.g., the third segment 335) of the tissue area 300 that is either not damaged by the ablation caused by the energy expended through ablation electrodes 412 and 414 at step 220 of the process 200 and the radioactive seed 440 deposited at the second segment 330, as shown in FIG. 5B. The radioactive seed 440 may have properties, as further disclosed herein, that may cause tissue area proximate to the radioactive seed 440 to be damaged, at step 250 of the process 200. As shown in FIG. 5C, the third segment 335 of the tissue area 300 may be damaged as a result of depositing the radioactive seed 440 at or near the FIG. 6 shows an illustration of a radioactive seed 600. Radioactive seed 600 may correspond to the radioactive seed 440 of FIGS. 4A-5C. The radioactive seed 600 may have a width W1 which is, for example, between 2 mm and 8 mm and, for example, 4.5 mm. As show, the radioactive seed 600 may include a capsule 610 outer shell that includes an internal gap area 620. The internal gap area 620 may include protective material that contains the radioactive source 630. Although shown as a particular oblong shape, the radioactive seed 600 may be round or any shape. The internal gap area 620 may be any applicable material such as a liquid, a gel, or the like. The radioactive seed 600 may be configured to dissolve, disintegrate, or otherwise allow the radioactive source 630 to damage tissue area where the radioactive seed 600 is deposited. Radioactive seeds may include any applicable material such as, iodine, palladium, or the like and may have any applicable marker such as a Tungsten marker. As an example, radioactive seeds may have an external length between 3 mm and 7 mm and/or an external diameter of between 0.5 mm to 1 mm.

According to an embodiment of the disclosed subject matter, the catheter needle 420 of catheter 400, as shown in FIGS. 5A-5C may be first extended to a greater thickness prior to being pulled back to a lesser thickness. As an example, the catheter needle 420 may be extended from an un-extended extension state P1 directly to the second extension state P2 into to the third segment 335 of the tissue area 300, as shown in FIG. 5C. One or more radioactive seeds (e.g., radioactive seed 440) may be deposited while the catheter needle 420 is at this grater extension state (e.g., P3 of FIG. 5C). Subsequently, the catheter needle 420 may be pulled back to a lesser extension state (e.g., P2 of FIG. Sb) and may deposit one or more radioactive seeds (e.g., radioactive seed 440) at the lesser thickness (e.g., second segment 330) of a tissue area 300.

According to an embodiment of the disclosed subject matter, a maximum thickness T3 of the tissue area 300 may be determined. The maximum thickness T3 of the tissue area 300 may be determined based on one or more of tissue mapping, an ultrasound, on a determination of the location of tissue area 300 (e.g., determining that the tissue area 300 corresponds to a VT), or the like. Based on determining the maximum thickness T3 of the tissue area 300, a determination of one or more extension states (e.g, P2, P3, etc.) of the catheter needle 420 may be determined. For example, the maximum thickness T3 may be a small enough that an ablation originating at the surface 310 of the tissue area 300 plus a first extension state P2 followed be depositing one or more radioactive seed(s) at the first extension state P2 may be sufficient to damage through the entire thickness of the tissue area 300 such that the tissue area 300 does not conduct electricity. According to this embodiment, one or more distances for catheter needle 420 extensions may be determined based on the maximum thickness T3 of the tissue area 300.

According to another embodiment, an ablation electrode (e.g., electrode 412 and/or 414) of a catheter 400 of FIG. 4 may be applied to the surface of a tissue area (e.g., tissue area 300 of FIG. 3) at step 210 of the process 200 of FIG. 2. Energy may be provided to the ablation electrode to ablate the tissue area (e.g., tissue area 300) starting at the surface (e.g., surface 310 of the tissue area 300), at step 220 of the process 200. A determination may be made that, after the ablation at step 220, a threshold thickness (e.g., the entire thickness of the tissue area) of the tissue area is not damaged such that electricity is conducted through at least part of the tissue area (i.e., the undamaged portion of the tissue area). Accordingly, based on the determination that the threshold thickness is not ablated through, steps 230-250 of the process 200 of FIG. 2 may be implemented. To clarify, if a determination is made that ablation did not damage the threshold thickness (e.g., entire thickness) of a given tissue area, then the catheter needle may be inserted into a thickness of the tissue area and a radioactive seed may be deposited at the thickness to damage the unablated portion of the tissue area. As disclosed herein, this process may be repeated for two or more thicknesses such that the threshold thickness (e.g., entire thickness) of the tissue area is damaged.

According to an embodiment, a determination may be made that electrical activity through a tissue area is below an electrical activity threshold after depositing the one or more radioactive seeds. Upon determining that the electrical activity through the tissue area is below an electrical activity threshold, the process 200 of FIG. 2 may be completed such that no steps are repeated. To clarify, the tissue in the tissue area may be sufficiently damaged such that no further ablation or radioactive seed deposition is required to prevent further electrical activity through the tissue area.

Although the examples provided herein are directed to cardiac conditions such as cardiac arrhythmias, it will be understood that the techniques and devices provided herein may be used to treat other conditions such as neuro conditions (e.g., focal epilepsy), cancer therapy (e.g., urology, breast cancer therapy, lung cancer therapy, etc.).

Any of the functions and methods described herein can be implemented in a general-purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer-readable media). The results of such processing can be mask works that are then used in a semiconductor manufacturing process to manufacture a processor which implements features of the disclosure.

Any of the functions and methods described herein can be implemented in a computer program, software, or firmware incorporated in a non-transitory computer-readable storage medium for execution by a general-purpose computer or a processor. Examples of non-transitory computer-readable storage mediums include a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

It should be understood that many variations are possible based on the disclosure herein. Although features and elements are described above in particular combinations, each feature or element can be used alone without the other features and elements or in various combinations with or without other features and elements.

The invention claimed is:

1. A device comprising:
   an ablation electrode;
   a catheter needle, the catheter needle comprising:
   a first hollow portion;
   a movement mechanism configured to extend the first hollow portion past an initial state;
   a radioactive seed reservoir configured to hold a plurality of radioactive seeds; and
   a release mechanism configured to provide at least a subset of the plurality of radioactive seeds from the radioactive seed reservoir to the first hollow portion.

2. The device of claim 1 further comprising a second hollow portion configured to irrigate fluid.

3. The device of claim 1, wherein the ablation electrode is configured to provide thermal energy.

4. The device of claim 1, wherein the movement mechanism is further configured to extend the first hollow portion to one or more of a plurality of extension states.

5. The device of claim 4, wherein the movement mechanism is further configured to retract the first hollow portion to the initial state from the one or more of the plurality of extension states.

6. The device of claim 1, wherein the radioactive seed reservoir comprises a radioactive seal.

* * * * *

UNITED STATES PATENT AND TRADEMARK OFFICE
CERTIFICATE OF CORRECTION

| | | |
|---|---|---|
| PATENT NO. | : 11,623,105 B2 | Page 1 of 1 |
| APPLICATION NO. | : 16/707572 | |
| DATED | : April 11, 2023 | |
| INVENTOR(S) | : Israel Zilberman et al. | |

It is certified that error appears in the above-identified patent and that said Letters Patent is hereby corrected as shown below:

In the Specification

In Column 1, Line 12, delete "(AF))" and insert -- (AFib)) --, therefor.

In Column 1, Line 66, delete "an tissue" and insert -- a tissue --, therefor.

In Column 3, Line 19, delete "disclosure" and insert -- disclosed --, therefor.

In Column 4, Line 55, delete "Carte" and insert -- Carto® --, therefor.

In Column 7, Line 34, delete "different" and insert -- differently --, therefor.

In Column 8, Line 37, delete "effected" and insert -- affected --, therefor.

In Column 9, Line 47, delete "FIG. 0.2," and insert -- FIG. 2, --, therefor.

In Column 10, Line 27, delete "show," and insert -- shown, --, therefor.

In Column 10, Line 49, delete "into to" and insert -- into --, therefor.

In Column 10, Line 54, delete "FIG. Sb)" and insert -- FIG. 5b) --, therefor.

In Column 11, Line 3, delete "be" and insert -- by --, therefor.

Signed and Sealed this
Twenty-first Day of November, 2023

Katherine Kelly Vidal
*Director of the United States Patent and Trademark Office*